United States Patent [19]

Garst et al.

[11] Patent Number: 5,420,295

[45] Date of Patent: May 30, 1995

[54] PROCESS FOR PREPARING 4,4-DIALKYL-6-HALO-CHROMANS OR THIOCHROMANS USEFUL AS PHARMACEUTICAL INTERMEDIATES

[75] Inventors: Michael E. Garst, Newport Beach, Calif.; Lloyd J. Dolby; Nestor A. Fedoruk, both of Eugene, Oreg.

[73] Assignee: Allergan, Inc., Irvine, Calif.

[21] Appl. No.: 183,543

[22] Filed: Jan. 19, 1994

[51] Int. Cl.$^6$ .................. C07D 335/06; C07D 311/58
[52] U.S. Cl. ....................................... 549/23; 549/398
[58] Field of Search .................. 549/23, 398

[56] References Cited

U.S. PATENT DOCUMENTS

| | | | |
|---|---|---|---|
| 4,739,098 | 3/1989 | Chandraratna | 560/8 |
| 4,810,804 | 4/1989 | Chandraratna | 514/311 |
| 5,023,341 | 6/1991 | Chandraratna | 549/23 |
| 5,089,509 | 2/1992 | Chandraratna | 514/337 |
| 5,162,546 | 11/1992 | Chandraratna | 549/23 |

FOREIGN PATENT DOCUMENTS

176034-B 8/1989 European Pat. Off. .

*Primary Examiner*—Nicky Chan
*Attorney, Agent, or Firm*—James M. Hoch; Robert J. Baran; Martin A. Voet

[57] ABSTRACT

A process of preparing intermediates useful in making compounds with retinoic acid-like activity is disclosed. The intermediates are halogenated chromans and thiochromans of the formula shown below and are prepared by the alkylation of a phenol or thiophenol with an alkene compound (the starting materials shown in the formula below), cyclization and halogenation.

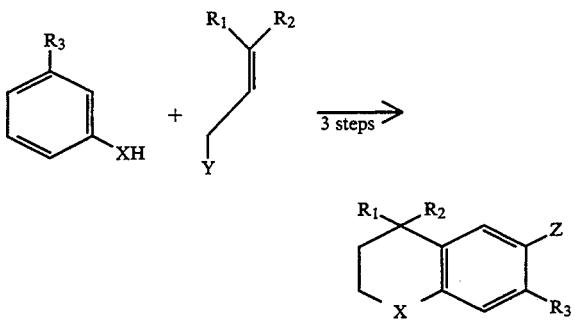

In the formula the symbols have the following meanings: $R_1$ and $R_2$ are $C_1$ to $C_4$ alkyl, $R_3$ is H or $C_1$ to $C_4$ alkyl, X is oxygen or sulfur, Y is a leaving group, and Z is chlorine, bromine or iodine.

9 Claims, No Drawings

PROCESS FOR PREPARING 4,4-DIALKYL-6-HALO-CHROMANS OR THIOCHROMANS USEFUL AS PHARMACEUTICAL INTERMEDIATES

FIELD OF THE INVENTION

The present invention is directed to the preparation of compounds which serve as intermediates in the preparation of molecules that possess retinoic acid-like biological activity. More specifically, the present invention is directed to intermediates which are useful in the production of 6-[(4,4-dimethyl-chroman-6-yl)ethynyl]nicotinic acids and esters or 6-[(4,4-dimethyl-thiochroman-6-yl) ethynyl]nicotinic acids and esters having retinoic acid-like activity.

BACKGROUND OF THE PRIOR ART

European patent application, EP-176,034-A discloses tetrahydronaphthalene compounds having an ethynyl-benzoic group. U.S. Pat. No. 4,739,098 discloses compounds wherein three olefinic units from the acid-containing moiety of retinoic acid are replaced by an ethynylphenyl functionality. These compounds have retinoic acid-like biological activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene (ethyne) group is a substituted phenyl group, and the second substituent is a substituted or unsubstituted chromanyl, thiochromanyl, or tetrahydroquinolinyl group. The compounds disclosed and claimed in U.S. Pat. No. 4,810,804 have retinoic acid-like biological activity.

Several U.S. patents issued to the same inventor and assigned to the same assignee as the present application disclose such disubstituted compounds wherein one of the groups is chroman, thiochroman or tetrahydroquinoline and the other is phenyl or pyridyl or another heterocycle. U.S. Pat. No. 5,089,509 describes chroman or thiochroman acetylene derivatives which have a pyridyl group as the other substituent. U.S. Pat. No. 5,234,926 discloses tetrahydroquinolin-ethynyl groups substituted by a monoheterocyclic group such as pyridine. U.S. Pat. No. 5,162,546 discloses (thio)chromanyl-ethynyl groups substituted by phenyl moieties. These three patents are hereby incorporated by reference in their entireties.

Retinoic acid-like activity has been generally recognized in the art to be associated with useful biological activity. Specifically, compounds having retinoic acid-like activity are useful as regulators of cell proliferation, and particularly as agents for treating dermatoses, such as ache, Darier's disease, psoriasis, icthyosis, eczema, atopic dermatitis and epithelial cancers, for treating arthritic diseases and other immunological disorders (e.g. lupus erythematosus) for promoting wound healing, for treating dry eye syndrome and for reversing the effects of sun damage to skin.

With respect to the synthetic processes of the present invention that involve the formation of compounds which are useful for coupling with an acetylenic (ethynyl) function to form the retinoid compounds disclosed in certain of the above cited Chandraratna patents, U.S. Pat. Nos. 5,023,341, 5,053,523 and 5,248,777 disclose processes and compounds useful for coupling to the intermediates prepared according to the process of the present invention and are hereby incorporated by reference in their entireties.

SUMMARY OF THE INVENTION

The invention is directed to a process of making a substituted chroman or thiochroman compound of formula IV

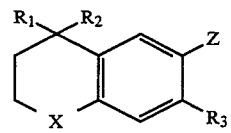

formula IV as shown in the sequence below wherein X is oxygen or sulfur, Z is chlorine, bromine or iodine, $R_1$ and $R_2$ are $C_1$ to $C_4$ alkyl, and $R_3$ is hydrogen or $C_1$ to $C_4$ alkyl, comprising, i) O-alkylating or S-alkylating a compound of formula I

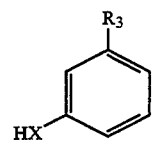

formula I wherein X and $R_3$ are as defined in formula IV with a compound of formula V

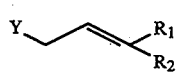

formula V wherein Y is a leaving group and $R_1$ and $R_2$ are as defined in formula IV, ii) cyclizing the alkylated product to form the bicyclic compound of formula III

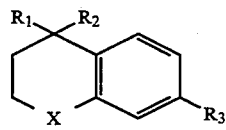

formula III wherein X, $R_1$, $R_2$ and $R_3$ are as defined in formula IV and iii) halogenating said bicyclic compound to give a compound of formula IV.

This process of making 4,4-dialkyl-6-halo chroman and thiochroman compounds which can optionally be substituted by alkyl at the 7-position comprises O- or S-alkylating phenol or thiophenol or suitably substituted alkyl derivatives at $R_3$ of formula I with an alkene compound via nucleophilic substitution, cyclizing the alkylated product of the alkylation step and then halogenating the resulting bicyclic compound. These compounds find use as precursors for coupling with an acetylene moiety and subsequent coupling with aromatic or heteroaromatic acids or esters to give compounds having retinoic-acid like activity which is pharmacologically useful.

Scheme 1 charts the new preparative sequence for making the halogenated intermediates and additionally shows the steps necessary for making the compounds previously disclosed by Chandraratna as having retinoic acid-like activity. The additional steps in making the retinoid compounds consist of coupling by means of a catalyst, the halogen intermediates prepared by the present invention with a silylated acetylene compound, removal of the silyl group and then coupling the other, now unsubstituted, end of the acetylene again by means of a similar type of catalytic reaction with a phenyl or heteroaryl ring which bears a halogen leaving group and an acid or ester substituent.

DETAILED DESCRIPTION OF THE INVENTION

The advantages of this novel synthesis include use of easily purified, readily available starting materials (phenol, thiophenol, m-cresol, or m-thiocresol, etc.) and an improved yield in the cyclization step, and an improved overall yield. The applicants have also found that, surprisingly, the electrophilic bromination is quite selective at the 6-position of the ring. This result is surprising in view of reactions with other small electrophiles in the 4,4-dialkyl-chroman or 4,4-dialkyl-thiochroman ring systems which give mixtures of regioisomers. This selectivity improves the yield of the desired isomer and obviates the need for separation of other, contaminating isomers in the reaction product.

Synthetic studies were performed on the electrophilic addition of dichloromethyl methyl ether to the 4,4-dimethyl thiochroman ring using Lewis acid catalysis (e.g. $SnCl_4$ or $TiCl_4$). Addition of dichloromethyl methyl ether to the aromatic ring followed by hydrolysis gave mixtures of aldehydes as products. The reactions were conducted as described in Example 8. In both parts of the example, part A using $SnCl_4$, and part B using $TiCl_4$, the predominant regioisomer was formed at the 8 position of the ring in preference to the 6-substituted isomer in the ratio of about 60:40. This preference for the 8-position in this reaction caused this possible route to formation of the substituted stilbene compounds of analogous structure to be abandoned.

Electrophilic halogenation of the same thiochroman ring systems does introduce bromine at the 6-position of the ring, almost exclusively. (A gas chromatogram of the reaction mixture in Example 3 showed there was about 5% of a contaminating compound in the reaction product that could be another brominated isomer.) As disclosed in the summary of the invention and is detailed in above mentioned example, the bromination reaction proceeded to give an 81% yield of the desired product.

The conditions under which the bromination is run have been studied to optimize the yield of useful product from the reaction. As a result, the applicants have found that maintaining the temperature of the bromination step between $-8°$ C. and $0°$ C. gives a more regiospecific product with little formation of other isomers.

Example 3 details an experimental method for bromination of the thiochroman ring using bromine and iron filings, however some halogenation reactions proceed in the absence of any promoter. (cf. Example 4). The method of electrophilic halogenation using the halogen source and a solvent, but no catalyst or promoter, is also contemplated in this invention.

The brominated reaction product is preferred for use in the catalytic coupling with the derivatized acetylenes to produce compounds such as the silylated 6-acetylene (thio)chroman of Scheme 1. However it is well-known in the art that chlorine and iodine function in the same manner as bromine in electrophilic additions to aromatic rings, and so, too, fall within the scope of the present invention. Owing to the differing reactivities of the halogens, different reagents and conditions may be used. Some examples of reagents that are promoters of electrophilic halogen substitution are metal salts of the halogens such as titanium tetrachloride ($TiCl_4$), tin tetrachloride ($SnCl_4$) or antimony trichloride ($SbCl_3$). The halogen counter-ion (in the foregoing examples the counter-ion is chloride) should be the same as the halogen being used in the reaction, otherwise "scrambling" of the halogen introduced in the reaction can result. If, for example, the compound is being brominated, then $TiBr_4$, $SnBr_4$ or $SbBr_3$ may be used in the reaction. N-chlorosuccinimide, N-bromosuccinimide and N-iodosuccinimide are also reagents that can provide electrophilic halogen for substitution reactions, however, they can also generate halogen free radicals which would not operate in the present invention. Experimental conditions which favor electrophilic substitution over free radical substitution are: lower reaction temperatures, absence of a UV or other strong light source and use of a solvent in the reaction. Conditions which favor free radical substitutions are: irradiation by UV light, high temperatures and/or gas phase reaction conditions. Typical solvents that are used in electrophilic halogenation reactions of this type are dichloromethane or other polar chlorinated solvents and glacial acetic acid or trifluoroacetic acid. The conditions usually employed in halogenation reactions are room (ambient) temperature to about $-20°$ C. and atmospheric pressure in the solvents listed above. The preferred conditions for halogenation in the present invention are those which favor electrophilic halogen substitution over free radical halogen substitution. More preferred are the reaction conditions within the temperature range of $-15°$ to $15°$ C., atmospheric pressure and a solvent such as dichloromethane or acetic acid. Most preferred is the condition where the temperature is maintained between $-8°$ and $0°$ C. In Example 4, an iodination reaction on the thiochroman ring is reported that uses iodine monochloride (ICl) as the reagent. In this example the chlorine atom bonded to iodine acts as a promoter for iodine substitution, owing to its greater electronegativity chlorine enhances the electrophilicity of the iodine atom. It is within the skill of the ordinary chemical artisan to determine the most advantageous conditions for electrophilic addition of chlorine, bromine or iodine to the chroman or thiochroman rings of the present invention.

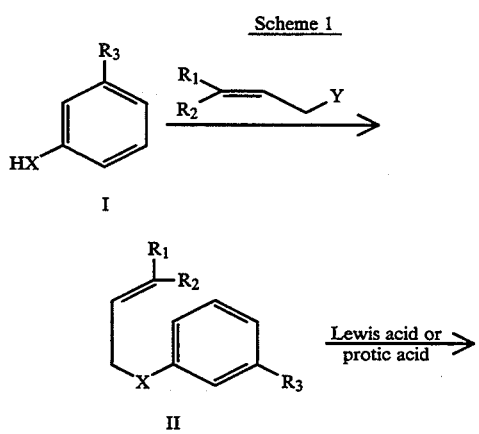

Scheme 1

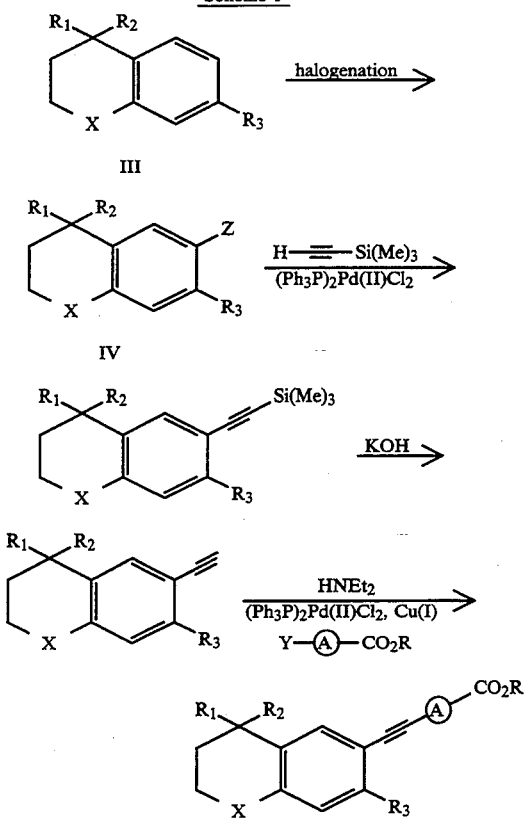

X = S, O
Y = leaving group
Z = Cl, Br, I
R = H, lower alkyl, metal cations
R$_1$, R$_2$, R$_3$ = C$_1$–C$_4$ alkyl (A) = phenyl, pyridyl, thienyl, furyl, pyridazinyl
pyrimidinyl, pyrazinyl, thiazolyl or oxazolyl With reference to the compounds of Scheme 1, the sequence illustrates a general synthesis of the halogenated intermediates. When X is sulfur and R$_1$ and R$_2$ are methyl or other C$_1$ to C$_4$ alkyl, the following reaction conditions may be used in obtaining the desired compound. A thiophenol (formula I) which may be substituted at R$_3$ (defined above as hydrogen or C$_1$–C$_4$ alkyl) is alkylated, preferably under strongly basic conditions such as NaOH in a polar solvent (e.g. acetone, room temperature) with a compound of formula II wherein R$_1$ and R$_2$ are methyl or other C$_1$ to C$_4$ alkyl, and Y is halogen, mesylate, tosylate, or another suitable leaving group. The resulting alkylated thiophenol (formula III) is thereafter cyclized under Friedel-Crafts or like conditions, typically by refluxing in an inert solvent such as benzene or toluene, preferably in the presence of phosphorous pentoxide and phosphoric acid. The resulting thiochroman (formula IV) may then be isolated by distillation.

The thiochroman may be dissolved in an inert chlorinated solvent such as methylene chloride, and iron filings may be added to the solution which is cooled, preferably to between −10° to 10° C. Bromine is introduced drop-wise into the cooled, stirred solution at such a rate as maintains the temperature between −10° to 10° C. over a period between 0.5 and 5 hr. After the bromine addition is complete the reaction mixture is stirred for another 0.5 hr and then a solution of sodium bicarbonate solution is added to the reaction mixture with stirring. The brominated thiochroman is recovered by extraction and other conventional means.

Alternatively, for the preparation of the chroman intermediate (formula IV, wherein X is oxygen and R$_1$ and R$_2$ are methyl) 3-phenoxypropionic acid or 3-(2-alkylphenoxy)propionic acid is used in the alkylation step. These materials may be prepared by O-alkylation of phenol or 2-alkylphenols with, for example, 3-chloropropionic add by means known in the art, or may be purchased. The carboxylic acid function may then be esterified by heating to reflux in an alcohol, preferably methanol, with an acid which is preferably p-toluenesulfonic acid. Addition of molecular sieves to capture water as it forms in the esterification allows a better yield of the carboxy methyl ester. Preferably the reaction may be run for about 24 hours at reflux or until it appears to be complete as determined by, for example, thin layer chromatography. The solvent is then removed under vacuum and the remaining oil may be purified by extraction and distillation.

The resulting methyl ester may then be dissolved in dry ether and added dropwise to methyl magnesium bromide in ether. The mixture is heated to reflux under an inert atmosphere for preferably sixteen hours, then may be quenched by addition of saturated NH$_4$Cl solution and the resulting phases are separated. The organic phase may be washed and dried and the solvent removed. Distillation of the resulting oil gives the pure tertiary alcohol, 1-(3-methyl-3-hydroxy)butoxybenzene.

1-(3-methyl-3-hydroxy)butoxybenzene may be converted to the cyclized chroman by dissolving in nitromethane and adding dropwise to a solution of anhydrous aluminum chloride (AlCl$_3$) in nitromethane. The mixture may be stirred at room temperature for preferably about 20 hours and then diluted with ether. The ether layer is separated and washed and dried. After removal of the solvent the remaining 4,4-dimethylchroman may be subjected to silica gel chromatography using 100% hexane to yield the pure product.

Analogous to the description of the bromination of the substituted thiochroman given above, the chroman may be brominated in an inert chlorinated solvent preferably in the presence of iron filings with drop-wise addition of bromine. An especially preferred condition for the reaction is that the temperature be maintained between −8° and 0° C.

In the prior art process for preparation of the compounds of the present invention, described in U.S. Pat. Nos. 5,023,341 and 5,053,523, and shown in Scheme 2, the bromine atom is present in the starting material. Some of these brominated starting materials can be purchased, such as p-bromo-phenol and p-bromo-thiophenol. Others can be made by one of ordinary skill in the art, by techniques such as bromination of m-cresol or m-thiocresol and separation of resulting isomers. However, the yield of cyclized product from the second step of reaction scheme 2 is fairly low. The bromine atom on the benzene ring at the position ortho to the point of cyclization tends to deactivate the ring to electrophilic addition in the second step and so results in lower yields in comparison to the cyclization step of the present reaction. Additionally these di- and particularly tri-substituted benzene compounds have the drawback of potential mixtures of regioisomers being formed.

Although only two steps are required in Scheme 2 to obtain the desired heterocyclic bromide, the overall yield of the reactions is less than has been obtained in the present invention. Examples 1, 2 and 3 taken together provide the brominated thiochroman in 62.7% overall yield, while the yield of the two step process starting with 4-bromothiophenol gives 4,4-dimethylthiochroman in a yield of 49% or less, depending on the particular reaction conditions in the cyclization step.

Scheme 2

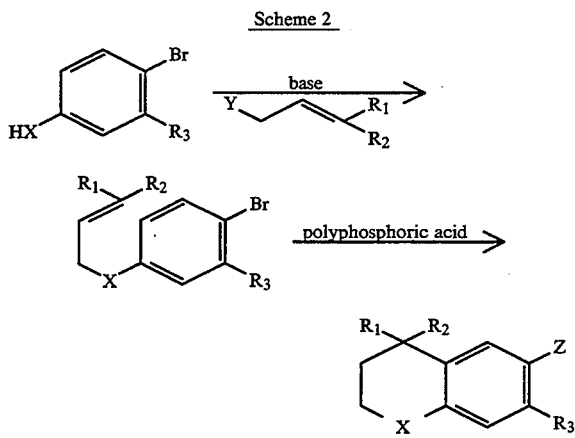

X = S, O
Y = leaving group
Z = Br
$R_1$ and $R_2$ = $C_1$-$C_4$ alkyl
$R_3$ = H or $C_1$-$C_4$ alkyl

[ Acetylenation and coupling to (hetero)aromatic acids or esters is effected as shown in Scheme I. ]

The invention is further illustrated by the following examples which are illustrative of a specific mode of practicing the invention and are not intended as limiting the scope of the appended claims.

EXAMPLE 1

Phenyl-3-methyl-but-2-enylsulfide

In a 5-L 4-necked flask fitted with a mechanical stirrer, two addition funnels and a thermometer was placed 2L of methanol and 330 g (3 moles) of thiophenol. A slow nitrogen purge was started and then, with stirring, a solution of 120 g (3 moles) of sodium hydroxide in water to make 350 mL and 447 g, 350 mL, (3 moles) of 1-bromo-3-methyl-2-butene were added from separate funnels at such a rate as to keep a slight excess of base. The addition required 1.5 hr. and the temperature reached 53° C. The mixture was stirred overnight in an outdoor lab where the temperature dropped to 10° C. Thin layer chromatography (hexane) showed a faint, fast-moving spot so the reaction was continued for another 24 hr. A saturated brine solution, 1.5 L, was added and the darker (upper) layer was separated. This layer was diluted with 400 mL of methylene chloride and then washed with 500 mL of water. The organic layer was stripped on a rotary evaporator, and the residue was heated under vacuum, 0.5 mm Hg.

EXAMPLE 2

4,4-Dimethylthiochroman

Into a 5-L flask fitted with a mechanical stirrer, condenser, and a nitrogen purge was placed 555 g (3.1 moles) of the just prepared sulfide, 743 g of 115% polyphosphoric acid, and 1300 mL of toluene. The mixture was heated on a steam bath for about 12 hr. The organic layer was decanted. Water, 1.5 L, was added to the residue and the organic layer was separated. The combined organic solutions were washed twice with 100 mL of 1N NaOH, once with 100 mL of saturated salt solution, dried over $MgSO_4$, filtered and stripped on a rotary evaporator. The residue was distilled through a Claisen head at 0.5 mm with a bath temperature of 120°–130° C. The product boiling at 83°–86° C. was collected. Gas chromatography (HP-5, 5% phenylmethyl silicone, 530 μ fused silica column 10 m long; initial temperature 100° C., programmed to 20°/min., flow rate 60 mL/min.) showed that this material was between 98.8–99.7% pure, retention time 3.0 min. The product turned pink in the receiver. The combined yield for two identical runs and a small preliminary run was 77.5% based on starting thiophenol.

EXAMPLE 3

4,4-Dimethyl-6-bromothiochroman

A 3-L 4-necked flask was equipped with an overhead stirrer, condenser connected to an HBr trap, dropping funnel and a thermometer. The flask was charged with 138 g (0.775 mol) of 4,4-dimethylthiochroman, 2 g iron filings and 1200 mL of methylene chloride and cooled to 3° C. Bromine (125 g, 0.778 mole) which was 99.5% pure, was added to the dropping funnel using 25 mL of methylene chloride to rinse in the last of the bromine. Dropwise addition of bromine was started and continued for 3 hr. as the temperature stayed below 8° C. After the bromine addition was complete, the reaction mixture was stirred for 30 minutes and then a solution of 84 g of sodium bicarbonate dissolved in 500 mL of water was added to the reaction mixture with vigorous stirring. The reaction mixture was transferred to a 3-L separatory funnel and the methylene chloride layer was separated. The sodium bicarbonate solution was extracted once with 300 mL of methylene chloride and then the combined methylene chloride layers were washed with 2×150 mL portions of water, dried over sodium sulfate and evaporated to give 190 g of crude yellow solid. A gas chromatogram run at this stage showed 89.3% 4,4-dimethyl-6-bromothiochroman, 4.5% of starting material and 5.3% of a peak showing slightly longer retention time than the 4,4-dimethyl-6-bromothiochroman (possibly an isomer of the desired product). The crude solid from above was dissolved in 600 mL of hot hexane, filtered and allowed to crystallize, first at room temperature and finally at freezer temperature. The off-white crystals weighed 139 g after drying, had a mp of 82-85° C. and were 100% pure by gas chromatography. A second crop was obtained by concentrating the hexane filtrate to 150 mL, allowing the mixture to cool to freezer temperature and then washing the filtered solid with 30 mL of cold hexane. A third crop of 8 g was obtained as above. All three crops were combined for an overall weight of 161 g (80.9% yield) of 4,4-dimethyl-6-bromothiochroman.

Following the procedures of Examples 1–3 in a similar manner, but substituting the corresponding alkylthiophenol for thiophenol and/or higher alkyl analogs for 1-bromo-3-methyl-2-butene (e.g. 1-bromo-3-ethyl-2-pentene which would yield 4,4-diethyl thiochroman if used in the above described synthetic sequence of Examples 1 and 2) the following compounds may be prepared:
- 4,4,7-trimethyl-6-bromothiochroman
- 4,4-dimethyl-6-bromo-7-ethylthiochroman
- 4,4-diethyl-6-bromothiochroman
- 4,4-diethyl-6-bromo-7-methylthiochroman In a manner similar to Example 3, but substituting the chromans described in Example 6 for the thiochroman, such 6-brominated compounds can be made as:
- 4,4-dimethyl-6-bromochroman
- 4,4,7-trimethyl-6-bromochroman
- 4,4-dimethyl-6-bromo-7-ethylchroman
- 4,4-diethyl-6-bromochroman
- 4,4-diethyl-6-bromo-7-methylchroman

EXAMPLE 4

4,4-Dimethyl-6-iodo-thiochroman 4,4-Dimethyl-thiochroman 5.0 g (0.0281 mol) was added into a 100 mL three-necked round bottom flask which had been outfitted with a mechanical stirrer, an addition funnel and an HCl trap and contained 25 mL of dichloromethane. The flask was cooled in an ice bath. ICl (available from Aldrich) was added in 5 mL of dichloromethane over a period of 5 min. and then was stirred for 20 min. One (1) mL of water was added to the reaction mixture and stirring was continued, after 10 min. 5 mL of $NaHCO_3$ solution was added. After 0.5 hr, a sample of the reaction mixture showed 67% of the mixture was starting material and 27% was product. After 2 hr this ratio was 55:41. The aqueous solution was tested and found to be strongly acidic and another 25 mL of $NaHCO_3$ solution was added which released copious amounts of $CO_2$, but the solution then had a pH of about 8. The reaction mixture was allowed to stir overnight and then was worked up with $NaHSO_3$ solution and then was washed with water. Removal of the solvent in vacuo gave 4.6 g of solid which gas chromatography showed to be 66% starting material and 33% 4,4-dimethyl-6-iodothiochroman (17.8% yield).

EXAMPLE 5

Methyl 3-phenoxypropionate

A solution of 3-phenoxypropionic acid (25 g, 150.4 mmol) and p-toluenesulfonic acid (1.23 g, 6.46 mmol) in 500 mL of methanol was heated to reflux under nitrogen atmosphere in a 1 L round-bottom flask though 3 Å, 8–12 mesh molecular sieves which is equipped with a soxhlet extractor and condenser. The mixture was heated at reflux for 21 hr and then cooled. Methanol was removed on a rotary evaporator to leave a light yellow oil which was taken up in 50 mL of water and then extracted with ether (3×75 mL). The combined ether extracts were washed with $NaHCO_3$ solution, water and brine and dried over $MgSO_4$. Removal of the solvent and then Kugelrohr distillation (80° C., 0.8 mm Hg) gave a yield of 26.26 g (97%) of the named product.

EXAMPLE 6

1-(3-methyl-3-hydroxy)butoxybenzene

A solution in dry ether (40 mL) of methyl 3-phenoxypropionate (25.7 g, 0.143 mol) was added dropwise under nitrogen atmosphere to a stirred solution of methyl magnesium chloride in THF (80 mL, 0.285 mol). The reaction mixture was allowed to stir at reflux under nitrogen for about 16 hr. The solution was then allowed to cool to room temperature and was quenched with saturated $NH_4Cl$ solution (about 125 mL). Additional ether was added to the solution, but the aqueous and organic phases did not separate. The emulsion was centrifuged and the emulsion separated into two phases. The ether layer was washed with 2×100 mL of brine and was dried over $MgSO_4$. The solvent was then removed to leave a light yellow oil. The oil was distilled through a Kugelrohr apparatus (at 80° C., 0.1 mm Hg) to obtain 18.6 g (72%) of 1-(3-methyl-3-hydroxy)-butoxybenzene.

In a similar manner, but substituting the corresponding 3-(2-alkyl)phenoxypropionic acid for 3-phenoxypropionic acid in Example 6 and or higher alkyl analogs of methyl magnesium chloride, e.g. ethyl magnesium chloride, which would yield 4,4-diethylchroman if substituted in the sequence of Examples 5 and 6 there may be prepared the following compounds:
- 4,4,7-trimethylchroman
- 4,4-dimethyl-7-ethylchroman
- 4,4-diethylchroman
- 4,4-diethyl-7-methylchroman

EXAMPLE 7

4,4-dimethylchroman

A solution of 1-(3-methyl-3-hydroxy)butoxybenzene (18.6 g, 0.103 mol) in 150 mL of nitromethane was added dropwise to a stirred suspension of anhydrous aluminum chloride (17.0 g, 0.127 mol) in nitromethane (90 mL) in a 1 L round-bottom flask. The reaction mixture was stirred for about 20 hours at room temperature and the ~9M HCl solution (250 mL) was added slowly. The mixture was allowed to stir for about 20 min. and then ether (100 mL) was added. The layers were separated and the organic layer was washed with water, 5% $NaHCO_3$ solution, and brine, and then dried over $MgSO_4$. Solvent was removed first on a rotary evaporator and then the resulting solution was further concentrated under high vacuum. The resulting oil was subjected to silica gel chromatography using hexane as eluant. 7.58 g (45%) of 4,4-dimethylchroman was recovered.

EXAMPLE 8

The following example is provided to show the procedural details and determination of product isomers and yields in an electrophilic addition reaction using a small molecule other than halogen.

4,4-Dimethyl-6-thiochromanyl-carboxaldehyde

A. In a three-necked, round bottom flask equipped with magnetic stirring, a thermometer, addition funnel and a condenser fitted with a drying tube was added 25 mL of dichloromethane which was then cooled to −8° C. Addition of $SnCl_4$, 14.6 g (0.056 mol) was followed by rapid drop-wise addition of the dichloromethyl methyl ether 4.2 g (0.036 mol). Next 4,4-dimethylthiochroman was added dropwise over 1 hr while keeping the temperature below 5° C. A deep red solution formed and after addition of the thiochroman was complete the solution was allowed to warm to room temperature. On reaching room temperature the solution was heated at reflux for 2.5 hr. The solution was then cooled and poured into ice water (150 mL). The phases were separated and the aqueous phase was washed twice with dichloromethane. The combined dichloromethane phases were washed with 3N HCl (100 mL) and then with water (200 mL), then filtered through phase separation paper and concentrated in vacuo. Gas chromatography of a sample of the material revealed two peaks neither of which were starting material in a ratio of about 60 to 40. After evaporation and drying of the material a proton NMR showed the presence of two aldehyde proton peaks, again with a ratio of about 60 to 40. Silica gel chromatography of the resulting product using 25% dichloromethane in hexane as eluant gave an incomplete isolation of isomers, however fractional recrystallization of some of the middle fractions collected gave 1 g of solid which had an NMR spectrum consistent with 4,4-dimethyl-thiochromanyl-8-carboxaldehyde. This was the predominant isomer formed in the reaction.

B. 4,4-dimethylthiochroman was dissolved in 50 Ml of dry CH2Cl2 and added to a three-necked round bottom flask which was fitted with a mechanical stirrer, a condenser and a dropping funnel. The reaction vessel was cooled in an ice bath and TiCl4 was added over 2 minutes. Dichloromethyl methyl ether was added dropwise from the addition funnel over 25 minutes. The addition funnel was washed with 10 mL of dichloromethane and this was added to the reaction mixture, and stirring was continued for another 5 min. at ice bath temperature. The ice bath was then removed and the reaction was allowed to stir at ambient temperature for another 30 min., then it was heated to 35° C. and allowed to stir for another 15 min. The mixture was worked up by dropping onto ice and separating the dichloromethane phase, the aqueous phase was washed two times with 50 mL of dichloromethane. The combined portions of dichloromethane were washed once with water and dried through phase separation paper. Solvent was removed in vacuo and the remaining yellow oil weighed 4.3 g. Analysis by gas chromatography as described in part A showed that oil consisted of 62% 4,4-dimethyl-thiochromanyl-8-carboxaldehyde and 38% 4,4-dimethyl-thiochromanyl-6-carboxaldehyde.

Several modifications of the above described compounds and processes, and application of the herein disclosed processes to numerous compounds beyond the specific examples set forth above, may be practiced by those skilled in the art without departing from the scope and spirit of the present invention. Examples 5, 6 and 7, which outline an alternate method for the preparation of the 4,4-dimethylchroman molecule, follow the fundamentals of the preparative sequence while adding an additional two steps for adding geminal alkyl substituents and are intended to further broaden the disclosure of the process of practicing the invention. Therefore, the scope of the present invention should be interpreted solely from the following claims, as such claims are read in light of the present disclosure.

What is claimed is:

1. A process of making a substituted chroman or thiochroman compound of formula IV

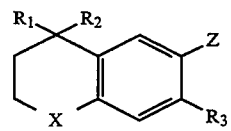

in the sequence set forth below wherein X is oxygen or sulfur, Z is chlorine, bromine or iodine, $R_1$ and $R_2$ are $C_1$ to $C_4$ alkyl, and $R_3$ is hydrogen or $C_1$ to $C_4$ alkyl, comprising, i) O-alkylating or S-alkylating a compound of formula I

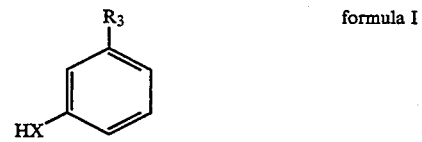

formula I wherein X and $R_3$ are as defined in formula IV with a compound of formula V

formula V wherein Y is a leaving group and $R_1$ and $R_2$ are as defined in formula IV, ii) cyclizing the alkylated product in the presence of a Lewis acid or a protic acid to form the bicyclic compound of formula III

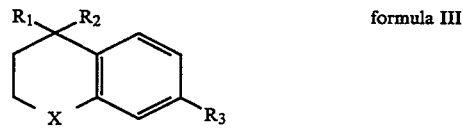

formula III iii) electrophilically halogenating said bicyclic compound to give a compound of formula IV.

2. The process of claim 1 wherein the halogenation in step 3 is effected with bromine.

3. The process of claim 1 wherein X is sulfur, $R_1$ and $R_2$ are methyl, $R_3$ is hydrogen or methyl and Z is bromine.

4. The process of claim 3 wherein $R_3$ is hydrogen.

5. The process of claim 1 wherein X is oxygen, $R_1$ and $R_2$ are methyl, $R_3$ is hydrogen or methyl and Z is bromine.

6. The process of claim 5 wherein $R_3$ is hydrogen.

7. The process of claim 2 wherein the temperature of the bromination is maintained between $-15°$ C. and $15°$ C.

8. The process of claim 2 wherein the temperature of the bromination is maintained between $-8°$ and $0°$ C.

9. The process of claim 1 wherein the compound of formula V has a leaving group represented by "Y" selected from the group consisting of chlorine, bromine, iodine, methanesulfonate, optionally substituted benzenesulfonate, trifluoromethanesulfonate, dialkylphosphate, and diarylphosphate.

* * * * *

UNITED STATES PATENT AND TRADEMARK OFFICE
CERTIFICATE OF CORRECTION

PATENT NO. : 5,420,295
DATED : May 30, 1995
INVENTOR(S) : Garst et al

It is certified that error appears in the above-indentified patent and that said Letters Patent is hereby corrected as shown below:

Column 8, line 55; delete "amp" and insert in place thereof -- a mp --

Signed and Sealed this

Fifth Day of September, 1995

Attest:

BRUCE LEHMAN

Attesting Officer     Commissioner of Patents and Trademarks